United States Patent [19]

Stetter et al.

[11] 4,384,925
[45] May 24, 1983

[54] GAS SENSING UNIT WITH AUTOMATIC CALIBRATION METHOD

[75] Inventors: Joseph R. Stetter, Naperville, Ill.; Lawrence Spritzer, Peekskill, N.Y.; Solomon Zaromb, Newark, N.J.

[73] Assignee: Becton Dickinson and Company, Paramus, N.J.

[21] Appl. No.: 200,107

[22] Filed: Oct. 24, 1980

[51] Int. Cl.³ .............................................. G01N 27/42
[52] U.S. Cl. .................................... 204/1 T; 73/1 G; 204/401; 204/406; 204/409; 340/632; 364/497; 364/571; 422/67; 422/98; 204/411
[58] Field of Search ................ 364/571, 497, 500; 204/195 R; 73/1 G, 1 R; 340/632; 422/67, 98

[56] References Cited

U.S. PATENT DOCUMENTS

| | | | |
|---|---|---|---|
| 3,437,446 | 4/1969 | Pierce | 422/98 X |
| 3,634,868 | 1/1972 | Pelavin et al. | 364/571 |
| 3,681,577 | 8/1972 | Gasiunas | 364/571 |
| 3,851,520 | 12/1974 | Schluter et al. | 73/1 G X |
| 4,001,103 | 1/1977 | Blurton et al. | 204/195 R |
| 4,151,739 | 5/1979 | Breuer et al. | 204/195 R X |
| 4,169,125 | 9/1979 | Rodriguez et al. | 364/497 X |

OTHER PUBLICATIONS

Buchanan, E. B., Jr., Talanta, vol. 27, pp. 947–954, Nov. 1980.

Primary Examiner—G. L. Kaplan

[57] ABSTRACT

Methods and apparatus are provided for sensing gases in the environment wherein electrochemical sensing procedures are utilized not only for monitoring ambient continuously for the presence of such gases; but also, for the periodic automatic recalibration and self-adjustment of the sensing instrument, as required, to accommodate changing conditions with time. Such accommodation includes not only changes in the instrument itself, but also changes in the environment affecting the accuracy of the monitoring function. The instrument is connected with a microprocessor, or other information storage or retrieval instrumentation which controls the periodic recalibration by measuring, separately from the monitoring function, the electrochemical response to a sample of the gas being monitored, and by adjusting the subsequent instrument readings to reflect the recalibration. During this recalibration procedure, the instrument can be adjusted to zero reading for accommodating drift, as will be understood. The microprocessor may be adjusted, also, to cause the automatic recalibration of the sensor instrument at preset intervals, as required at the location where it is being used.

Thus, the instrument of the invention has the ability to perform a calibration without the need for an operator or calibration gas. The requirement is that the instrument be sensing the gas of interest at the time of calibration.

7 Claims, 6 Drawing Figures

GAS SENSING UNIT WITH AUTOMATIC CALIBRATION METHOD

BACKGROUND OF THE INVENTION

This invention relates generally to gas detector units for monitoring noxious gases in the environment in the area where the units are placed so that persons involved in the environment where the instruments are located may be warned of the presence of a too high level of a noxious gas. More particularly, this invention relates to such a gas sensing unit which has incorporated therein provisions for recalibration of the instrument automatically at periodic intervals without the need for specific recalibration by an individual. That is, the instrument is controlled by a connected microprocessor-type instrument which controls the periodic recalibration of the gas sensing unit. By proper control through the microprocessor, various valve connections may be operated to cause the gas sensing unit to separate from its usual monitoring function and to calibrate through specific procedures, so as to accommodate changes in the instrument over a period of time and changes in the environment where it is functioning. The recalibration is incorporated into the microprocessor so that subsequent monitoring readings are automatically adjusted to reflect the recalibration. This invention is an improvement over the inventions described in U.S. Pat. Nos. 3,992,267, issued Nov. 16, 1976; 3,824,167, issued July 16, 1974; 3,776,832 issued Dec. 4, 1973 and 3,909,386, issued Sept. 30, 1975. Each of these patents is incorporated by reference in its entirety herein.

With ever increasing concern about pollution of our environment and our increasingly sophisticated knowledge with respect to the presence of polluting materials in the environment, attempts have been made to develop systems which will protect us by warning of increases in the concentration of certain substances in the ambient to a level which is toxic and/or otherwise dangerous to our existence. One such device which has been developed in recent years is a gas sensor operated through an electrochemical cell for sensing the presence of such gases adjacent a work area such as, for example, a mine shaft. As will be appreciated, it is important that such sensors continue to operate over a period of time so that certain enclosed areas are protected where certain levels of concentration of gases may cause death if exposure is for a specific period of time. It is important, also, from a manpower standpoint that the instruments need not be continuously attended to because of any rapid deterioration of the sensing capacity thereof. However, electrochemical gas sensors, for example, are subject to certain limitations over a period of time merely because of the chemical nature in which they operate, in the sense that the sensing capacity changes with environmental conditions.

Thus, there is a need with respect to present day instruments for maintenance at periodic intervals, and especially recalibration thereof. That is, such instruments change their performance characteristics over a period of time and it is necessary that they be recalibrated so as to restore accuracy. For example, presently carbon monoxide monitors which are placed around a hazardous area such as a blast furnace for monitoring, for example, 100–600 ppm CO are being calibrated once a month by a maintenance routine which requires an operator to visit each instrument installed for this purpose. The operator carries a certified calibration gas mixture of carbon monoxide and air which is typically 250 parts per million carbon monoxide/air. The certified span gas mixture is injected into the instrument to verify its response, and an adjustment is made in the instrument sensitivity, if required.

STATEMENT OF THE INVENTION

With this invention, by contrast, vastly improved sensor performance characteristics are achieved in the sense of gaining repeatability of the signal magnitude and zero selectivity and long-term stability of the system's performance by connecting the sensor to a conventional microprocessor or other programmable instrumentation which is programmed to monitor the sensor performance and, depending upon the program placed in the microprocessor, determines on a set periodic basis when the sensor is to be recalibrated. At that point, the sensor cell may be disconnected from the monitoring function and a set programmed sequential recalibration procedure takes place controlled by the microprocessor connected to the sensor unit and its associated valving structures. The recalibration procedure comprises measuring the sensor signal in response to a specific gas sample, establishing the concentration of the sensed gas in said sample, and storing in the microprocessor the values of said signal and of said concentration. This sequence is carried out automatically by the pre-programmed microprocessor. Based on said values, the microprocessor recalibrates the sensor to incorporate the new readings and extrapolates those new readings into the subsequent monitoring readings being taken by the sensor.

Also, as mentioned above, this recalibration procedure may be arranged to be carried out at preset intervals of, perhaps, once a week or once a month, depending upon the gas being monitored and the environment where it is being monitored.

Of course, the methods and apparatus of the invention here are not limited to the specific arrangement wherein the gas sensor cell is stopped from its monitoring function during the recalibration procedures. Arrangements may be made, in accordance with this invention, to include in a sensing unit at a particular location, a separate gas sensing cell which operates chiefly to carry out the recalibration function, while the main cell is maintaining the monitoring function during this period of time. In this way, the monitoring function is never interrupted and this is particularly important in instances where the location involved is exposed to a highly toxic gas. Again, with such an arrangement, a microprocessor is coordinated with both cells to institute the recalibration function of one sensor cell while maintaining the other sensor cell in its monitoring function. Subsequent to the recalibration of one sensor, the microprocessor incorporates and extrapolates the calibrated information into the monitoring function of the other sensor. As will be apparent to practitioners in the art, other arrangements may be made, in accordance with this invention, for the automatic recalibration procedure for determining coulometrically the current conditions for sensing a specific gas, according to the location and requirements of the instrument involved.

The invention also includes provisions for supplying, again automatically, a sample of gas for the periodic automatic recalibration of the instrument. That is, in certain instances, the concentration of monitored gas present in the ambient may not be sufficient to provide the appropriate readings for recalibration purposes. Under these circumstances, a separate unit may be interconnected with the sensor and the microprocessor for the purposes of supplying on a periodic basis as needed an adequate sample of the gas being monitored from a specific source so as to provide a sufficient quantity of the gas for the calibration procedure. For example, in a gas sensing situation where carbon monoxide is being monitored, frequently a low carbon monoxide content is present in ambient. Such a low carbon monoxide content may not be sufficient to carry out the automatic calibration procedures with the desired degree of accuracy. Thus, carbon monoxide may be produced in a separate attached instrument wherein the anodic electrolysis of water produces hydrogen ions which react with a sodium formate solution to produce the required carbon monoxide for the automatic recalibration procedure.

Thus, with this invention, a supply of a sample gas may be provided or generated so that the proper recalibration of the instrument takes place even though, at any one time, there may not be a sufficient concentration of the gas being monitored to carry out the automatic recalibration of the instrument as required.

With the foregoing and additional objects in view, this invention will now be described in more detail, and other objects and advantages thereof will be apparent from the following description, the accompanying drawings, and the appended claims.

IN THE DRAWINGS

Figure 4:
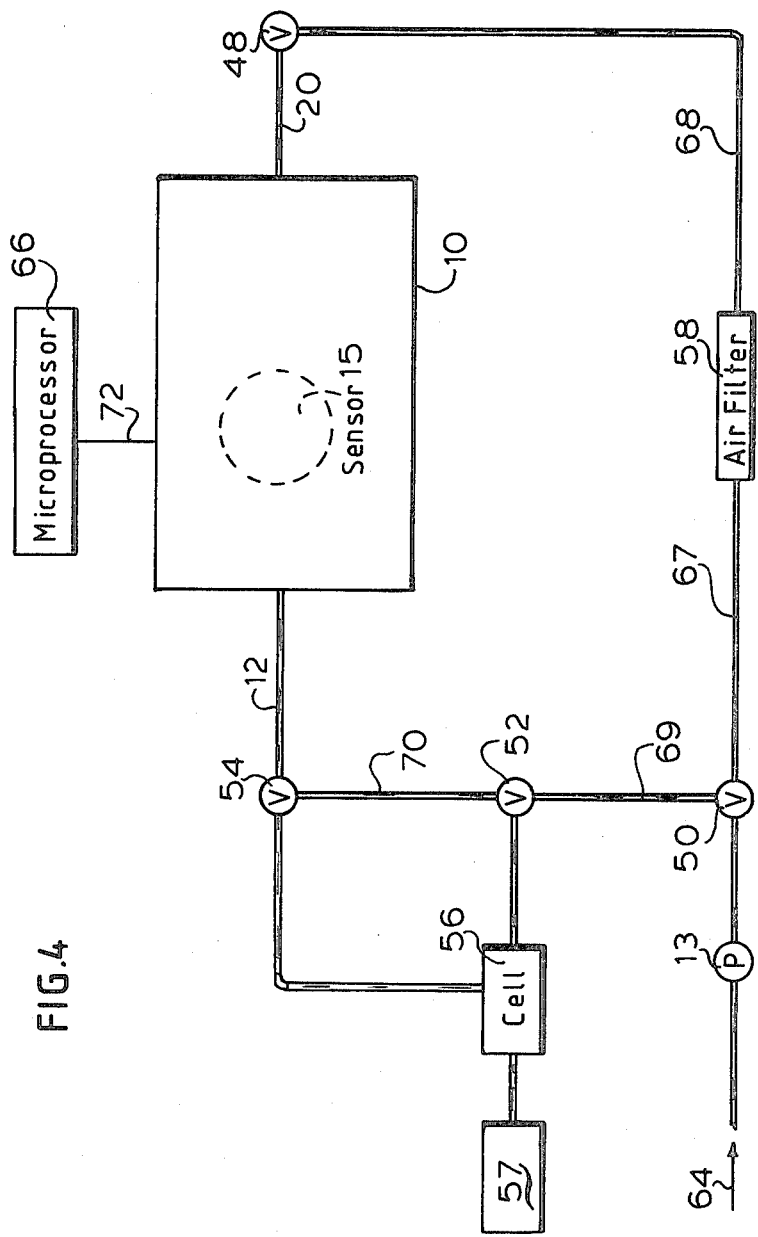
FIG. 4 is a diagramatic illustration in block form of an alternative arrangement of apparatus illustrating the invention herein wherein a separate unit is connected for providing a sample of gas for carrying out the automatic recalibration of the sensing unit.
Figure 5:
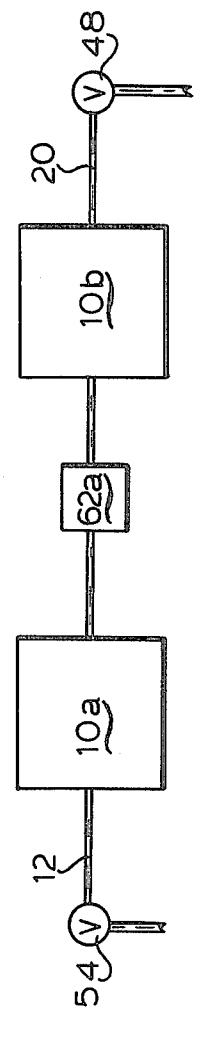
Figure 6:
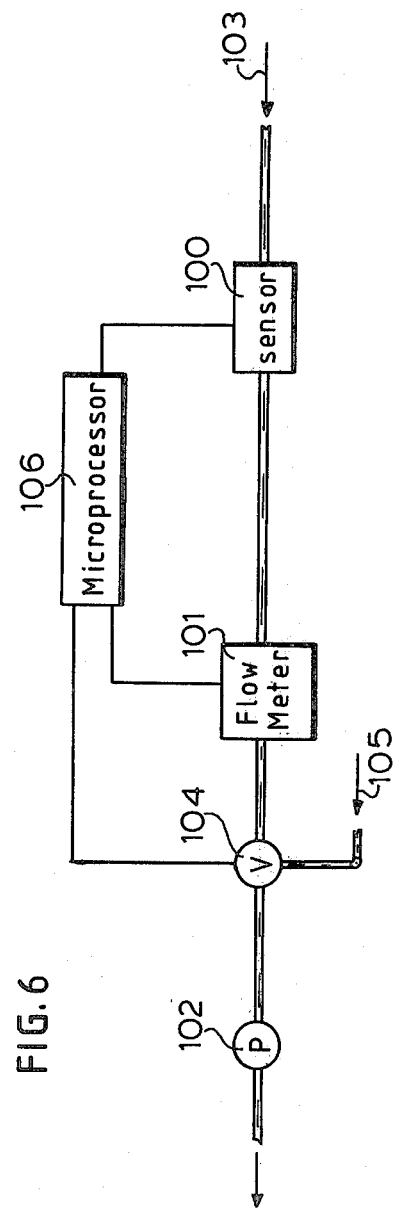

FIG. 5 is a diagramatic view similar to that in FIG. 4 showing yet another arrangement wherein two sensing cells may be incorporated in series with a flow meter and electrically actuated valves are provided for reversing flow between the two cells for carrying out the automatic recalibration of the sensing unit; and FIG. 6 is a block diagram of still another arrangement wherein automatic recalibration is achieved with a single sensing cell using at least two different gas flow rates.

DETAILED DESCRIPTION OF THE INVENTION

Referring to the drawings, in which like reference characters refer to like parts throughout several views thereof, a gas detecting device for the measurement of noxious gases is positioned within a housing 10. The device includes a sample intake means 11 in direct communication with line 12 for feeding the gas being monitored to the sensor 15 (electrochemical cell) which, in turn, is connected with a flow meter 17. Gas flowing through sensor 15 exits through exhaust outlet 20. Valve 19, positioned between flow meter 17 and outlet 20 may be provided to control the flow of gas exiting from the unit. The sensor is provided with a potentiostat 24 for maintaining a fixed relative potential between the sensing electrode and the reference electrode of sensor 15, and with a voltmeter 26. The potentiostat is hooked up to an electronic circuit described in the afore-mentioned patents.

Figure 1:
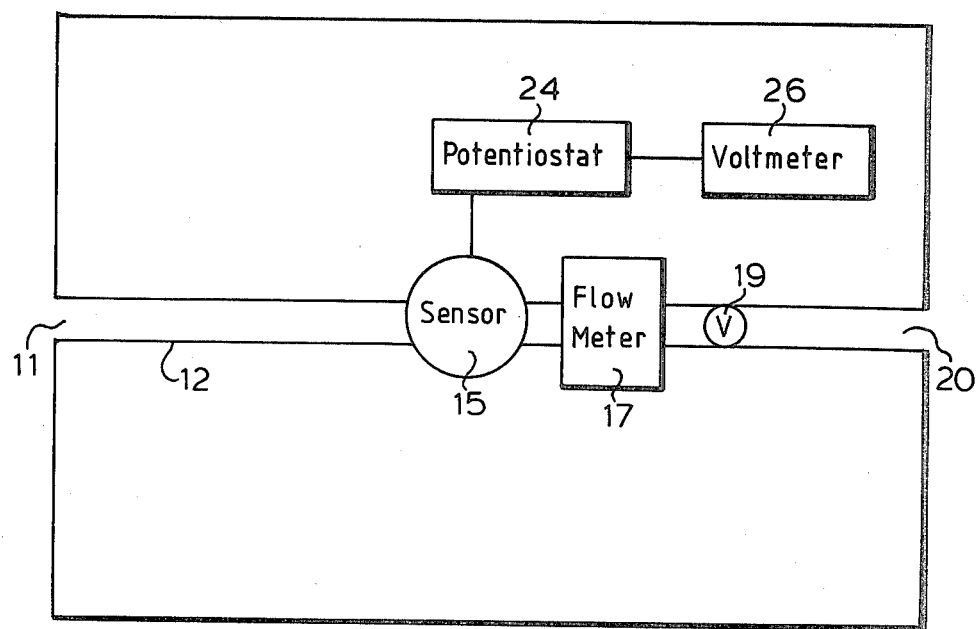
FIG. 1 is a diagramatic view in block form of a gas sensing unit illustrating the invention.
Figure 2:
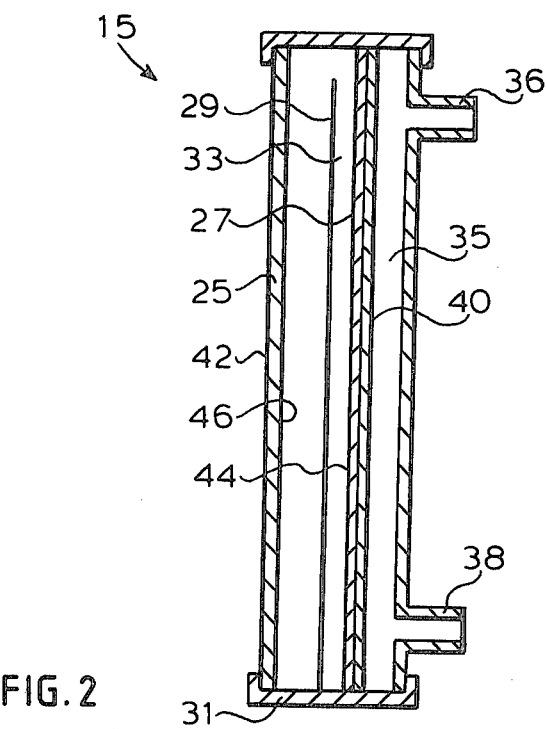
FIG. 2 is a cross-sectional view of an electrochemical cell for a gas sensing unit of the invention.

One form of electrochemical sensor which may be used in accordance with this invention is shown in FIG. 2 and includes a counterelectrode 25, a sensing electrode 27 and a third or reference electrode 29, all positioned within a housing 31. In the embodiment shown in FIG. 2, the counterelectrode, sensing electrode and third electrode are in contact with a free-flowing aqueous electrolyte 33. The nature of the electrolyte will be chosen, as will be understood by practitioners in the art, according to the gas being sensed in a particular location. Adjacent sensing electrode 27 is a reactant chamber 35 having an inlet 36 and an outlet 38. Counterelectrode 25 is in direct communication with atmospheric air. Both the sensing and counterelectrodes are light-weight electrodes comprising a hydrophobic plastic substrate (polytetrafluoroethylene) 40, 42, respectively, in a direct contact with reactant chamber 35 in the case of sensing electrode 27, and with the ambient environment in the case of counterelectrode 25. Catalytic film layers 44, 46, respectively, have been arranged on the hydrophobic plastic substrate by various procedures such as, for example, vacuum vapor deposition to a desired thickness as required. These catalytic film layers are in contact with the electrolyte of the cell, as will be understood. The reference electrode 29 may be a porous electrode comprised of a polytetrafluoroethylene substrate with an appropriate metallic catalytic film disposed thereon. A fixed potential of within the range of between about 0.4 and 1.5 volts relative to the standard hydrogen electrode depending upon the gas to be detected, is maintained on the sensing electrode by means of the reference electrode through the potentiostat 24. For further details concerning the arrangement of the imposed fixed potential on the sensing electrode, references are made to the above-noted patents.

Figure 3:
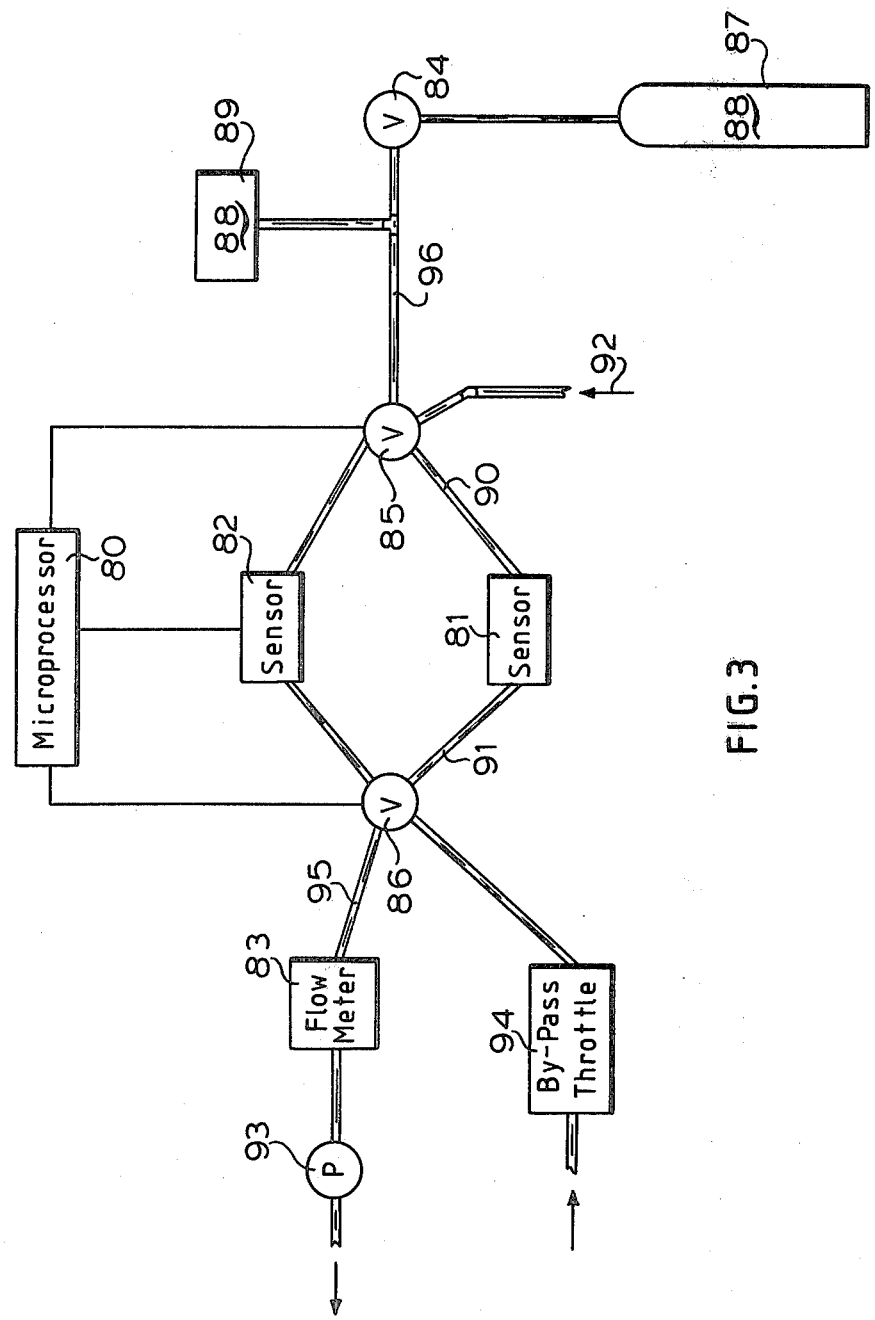
FIG. 3 is a schematic block diagram of a gas flow circuit for periodic recalibration of the cell illustrated in FIG. 1, according to one embodiment of the invention.

In one embodiment of the invention illustrated in the block diagram of FIG. 3, a microprocessor 80 records and stores the signals (i.e., voltage or current outputs) from two electrochemical sensors 81 and 82, and from a mass flowmeter 83, and also controls three electrically actuated valves 84, 85, and 86. (The term "microprocessor" as used herein is for the purpose of designating any form of instrumentation including any simple electronic instrumentation which will function to store information and control in a simplified manner the opening and closing of a number of solenoid valves, for example, in sequence to control the valving functions of the apparatus herein. One representative such instrument is Model Number HP9815A manufactured by the Hewlett Packard Company which is a programmable calculator, with appropriate connections for accessory instruments.) Sensor 82 serves during the usual continuous monitoring purposes, while sensor 81 remains idle most of the time and takes over the monitoring function only during the relatively brief periods during which sensor 82 is being calibrated. When sensor 81 is in the idle state, any access of air thereto is cut off by valves 85 and 86. Ambient air is then pulled by pump 93 through inlet 92 and valve 85 into sensor 82, and then through valve 86 and flowmeter 83. To provide approximately constant air flow through sensor 82, a by-pass throttle 94 is also connected to the flow circuit by valve 86 whenever circulation through sensor 81 is shut off.

Any small amounts of the measured pollutant trapped in the lines 90 and 91 connecting to sensor 81 and in its reactant chamber 35 (FIG. 2) at the start of the idle state are gradually consumed at its sensing electrode 27 (FIG. 2), and become insignificant, usually within the first 10 minutes, so that the signal from sensor 81 during most if its idle period yields the "zero" or "background" signal $S_1°$ of this sensor. To calibrate sensor 81, the normally closed valve 84 is first caused by microprocessor 80 to be opened for a predetermined short period of time so as to permit a sample of calibrating gas 88 from a compressed gas bottle 87 to enter an expansible bag 89. The capacity of bag 89 may be between 1 and 10 liters, for example. Gas 88 contains a previously calibrated concentration of the noxious pollutant detected by sensors 81 and 82 and the value of this calibrated concentration is stored in the memory of processor 80. Once bag 89 has been filled with gas 88, valve 84 is closed, and valve 86 causes throttle 94 to be closed off and the outlet line 91 of sensor 81 to be connected to the line 95 leading to flowmeter 83 and pump 93, while valve 85 causes the inlet 90 of sensor 81 to be connected to the line 96 leading to bag 89. The steady-state signal from sensor 81 can then be translated by the micoprocessor into a calibrated response constant $k_1$ for sensor 81. Given the background signal $S_1°$ and the response constant $k_1$, sensor 81 is ready to take over the monitoring function while sensor 82 is being calibrated.

Bag 89 is completely emptied following each calibration to prevent a gradual excessive gas build-up therein during repeated calibrations. Full evacuation of bag 89 is recognized by the microprocessor through a sharp decrease in the signals from the calibrated sensor and from flowmeter 83, whereupon valve 85 is actuated to disconnect the calibrated sensor from line 96, and to connect it to the ambient air inlet 92. The calibrated sensor thereupon assumes the monitoring function.

To calibrate sensor 82, valves 85 and 86 are actuated to shut off circulation to sensor 82 and to connect throttle 94 to line 95, thereby bringing sensor 82 into the idle state. After about 10 minutes or more, the background signal $S_2°$ of sensor 82 is recorded and stored in the microprocessor memory, and the afore-described calibration procedure may be repeated for sensor 82 to yield the corresponding response constant $k_2$. Sensor 82 is then caused to resume its monitoring function, while sensor 81 is returned to its idle state.

Of course, as will be understood by practitioners in the art, it is also possible to have sensors 81 and 82 share the monitoring functions for approximately equal time intervals.

As further illustrative of the invention herein, one may note FIG. 4 in which a diagramatic illustration in block form of another arrangement of apparatus illustrating the invention is shown. In the form of instrumentation shown here, an intermittent scheme of recalibration of a gas sensing instrument is illustrated. Thus, ambient air from source 64 is drawn by pump 13 into the system with the flow through the various lines being controlled by valves 48, 50, 52 and 54, with the functioning of the valves being under the control of a microprocessor 66.

In this case, valves 50, 52, 54 and 48 may be set to allow circulation of ambient air to be monitored through lines 69, 70, 12 and into sensor 15 contained in the instrument 10, and thereafter through line 20 to exit through valve 48. At one point, valves 54 and 48 are closed in order to segregate the air being sensed in sensor cell 15 in unit 10. In this connection, unit 10 may contain two sensor cells, with one for the purposes of a continued monitoring of ambient air from source 64 under the direction of the pump 13, while the second separate cell within housing 10 is for the specific purpose of the coulometric measurement of a segregated specific quantity of the air to be measured by the instrument. If such an arrangement is made, there will be a separate valving arrangement under the operation of the microprocessor 66 for segregating the coulometric cell for this separate measurement.

In any case, once the segregation procedure has taken place under the direction of the microprocessor, the microprocessor computes the number of coulombs generated from the segregated volume of air being measured, and the resulting reading in parts per million of, for example, carbon monoxide is determined, and thereafter calibrated into the readings of the microprocessor. Further, for a blank determination of the coulombs generated after CO has been removed from the air sample, valve 50 may be caused, along with valves 52, 54 and 48, to shunt air through the zero air filter 58, valve 48, the sensor cell in housing 10, and through valve 54.

The difference between the numbers of coulombs generated with and without the measured pollutants present in the sampled air is an absolute measure of the concentration of said pollutant within the segregated sample, provided that the volume of the sample and the ambient pressure and temperature are also given, and assuming approximately 100% faradaic efficiency for the reaction of the pollutant at electrode 27 (FIG. 2). The sample volume can be established during manufacture of instrument 10 and should not significantly change with time. The pressure and temperature can be measured by appropriate transducers and stored in the microprocessor memory. By comparing the value of the coulometrically determined concentration with the sensor signal just before segregation of the sample, the microprocessor can compute the sensor response constant, as in the embodiment of FIG. 3.

As a further feature of the invention herein and in those instances wherein there is not a sufficient concentration of the gas being monitored in ambient for the automatic recalibration of the instrument to take place, electrochemical generation of the sensed gas may be carried out in an electrochemical generation cell 56. For this purpose, ambient air is passed through cell 56 under the direction of valves 52 and 54 so as to supply through line 12 air with sufficient quantity in parts per million of carbon monoxide for the cell in housing 10 to effectively measure for the purposes of automatic recalibration. Again, after sufficient air with an elevated carbon monoxide content has passed into the sensor cell in housing 10, valves 54 and 48 operate to close off the cell for the recalibration purpose. As will be understood, the electrochemical generation cell 56 operates from a current source 57.

As stated above, various gases to be measured may be developed electrochemically for the purposes of automatic recalibration of a sensing system, in accordance with this invention, in those instances where there is not a sufficient concentration of the gas being sensed ordinarily in the ambient air being monitored. For example, formaldehyde may be generated by injecting dichloromethane in an aqueous alkaline solution. Alternatively, formaldehyde may be generated electrochemically by cathodic reduction of formic acid at a lead electrode at a low current density, or by cathodic reduction of oxalic acid in aqueous sulfuric acid solution at a lead, carbon or mercury electrode. Ethylene oxide may be formed by the reaction of ethylene chlorohydrin with an alkaline solution. Alternatively, it may be generated by electrochemical oxidation of ethylene at a zinc/zinc oxide anode in an aqueous sodium benzoate, tungsten oxide, or potassium carbonate solution. Hydrazine may be generated by the reaction of urea with sodium hypochlorite.

As further illustrative of the invention herein, one may note FIG. 5 which shows a further form of instrumentation for carrying out the invention here. In this case, two sensors are incorporated in housings 10a and 10b and the currents from both are monitored, while flow is through both sensors in series in one direction. At some point in time, the flow is reversed and the gas being sensed passes through the two sensors in the opposite direction. In this connection, a mass flowmeter 62a measures the flow through the two sensor units as controlled by the microprocessor 66 through an appropriate electrically activated valving arrangement, as will be understood.

As discussed previously above, the invention contemplates the use of two sensors operating under the control of the microprocessor 66 in which one sensor is used continuously as the monitoring sensor for monitoring the ambient where the unit is operating. A second sensor is segregated from this monitoring function and used solely for the purpose of the automatic recalibration of the instrument on a periodic basis, as desired. Such an arrangement may include, in accordance herewith, a two-sensor system wherein a single sensor unit is provided with a five electrode system. Under this arrangement, there are two sensing or working electrodes, each with an independent gas exposure chamber, and two counterelectrodes with one each connected to operate with one of the sensing electrodes, and with a single reference electrode connected to both of the sensing electrodes. In this case, one of the sensing electrodes and its associated gas exposure chamber is used for the continuous monitoring function, while the other is used only periodically, under the control, again of microprocessor 66 for the purposes of periodic recalibration. With this arrangement, a single electrolyte chamber is used and provisions must be made to prevent or minimize "cross-talk" between the electrodes via the electrolyte chamber in such a system.

Yet another embodiment of the invention is illustrated in FIG. 6. In this arrangement, a single sensor 100 is connected in series with a mass flow meter 101 to pump 102 via valve 104. To measure the zero background signal, valve 104 connects a by-pass air inlet 105 to pump 102, while disconnecting the flow meter 101 from the pump. Once the zero signal S° has been measured and recorded, valve 104 connects flow meter 101 and air inlet 105 to pump 102, thereby effecting an intermediate rate of flow of the monitored gas entering through sample inlet 103 into sensor 100. After recording the signals from sensor 100 and flow meter 101 at the intermediate flowrate, the microprocessor 106 causes valve 104 to close off the bypass inlet 105, thereby increasing the flow through sensor 100 to the maximum rate. After recording the sensor and flow meter signals at the maximum flowrate, the processor computes from the recorded data a newly recalibrated sensor response constant $k_u$ (corresponding to the usual flowrate) and uses this constant together with the latest S° value to compute the concentration of the sensed gas as the sensor signals are being recorded in the course of regular monitoring.

Thus, as will be apparent from the foregoing, there are provided, in accordance herewith, methods and apparatus for continuously monitoring and sensing of toxic gases in various environments with the instruments provided being so constructed and maintained as to continuously monitor without the need for periodic manual readjustment and recalibration of the instrument. With the arrangements herein, the instrument may be mounted and properly instrumented and programmed to readjust itself on a periodic basis, with the period of readjustment also being determined as desired and according to the particular location so as to continuously monitor for any dangerous toxic gases in the environment. In addition, the instrument may be arranged to recalibrate itself to accommodate such variables as degradation of the instrument itself and changes in the conditions under which monitoring is taking place at any one time. As will be appreciated, the elimination of periodic manual adjustments reduces substantially the cost of maintenance of such instruments, particularly in remote locations.

While the methods and apparatus herein disclosed form preferred embodiments of this invention, this invention is not limited to these specific forms of method and apparatus, and changes can be made herein without departing from the scope of the invention which is defined in the appended claims. For example, other forms of sensor cells may be chosen by practitioners in the art, such as those referred to in the prior art patents noted above, so long as provision is made for a procedure to be carried out under the control of selected instrumentation for automatic recalibration of the instrument on a periodic basis, as required under the circumstances of the environment in which the instrument is being used.

What is claimed is:

1. Self-calibrating electrochemical sensor apparatus for continuously monitoring and detecting an electrochemically active gas comprising
   (a) a housing;
   (b) an aqueous electrolyte contained in said housing;
   (c) a sensing electrode substantially continuously in contact with said electrolyte and the ambient fluid around said apparatus to be monitored which may contain an electrochemically active gas;
   (d) a counterelectrode in contact with said electrolyte;
the improvement characterized by
   (e) automatic control means connected to said apparatus;
   (f) means in said automatic control means for controlling and measuring the flow of ambient fluid to said apparatus;
   (g) said controlling and measuring means including means for segregating a specific sample of ambient fluid, said segregated sample being of unknown concentration of any electrochemically active gases contained therein;
   (h) said segregating means including
      (1) a first reactant chamber in contact the said sensing electrode and having a first ambient fluid inlet and a first ambient fluid outlet;
      (2) a second reactant chamber in contact with a second sensing electrode having a second ambient fluid inlet and a second ambient fluid outlet;

(3) said first and said second inlets and outlets being connected in series;

(4) a pump and valving system for causing flow of said segregated sample of fluid through said first chamber and then into said second chamber, and then causing reversed flow whereby the said segregated sample of fluid is caused to flow first through said second chamber and then into said first chamber;

(i) a flow meter in said controlling and measuring means for measuring the rate of flow past said sensing electrode of a sample of an ambient fluid being monitored;

(j) means in said automatic control means for measuring the signal from said sensor apparatus in response to said segregated sample;

(k) means in said automatic control means for establishing the concentration of an active gas in said segregated sample;

(l) means in said automatic control means for storing the values of said signal and of said concentration; and (m) means in said automatic control means for adjusting the calibration of said sensor apparatus according to the values of said storing means during said continuous monitoring and detecting thereof.

2. The apparatus of claim 1, further characterized by
(a) a reference electrode in contact with said electrolyte; and
(b) electrical communication means between said reference electrode and said sensing electrode for selectively establishing a fixed potential on said sensing electrode.

3. The apparatus of claim 1, further characterized by
(a) said automatic control means is a microprocessor.

4. A method for the automatic recalibration of a gas sensing and monitoring unit which is in continuous monitoring and sensing operation, characterized by the steps of
(a) connecting a gas sensor unit to an automatic control;
(b) placing said gas sensor unit in an area to be monitored;
(c) establishing a first and a second gas sensing area in said gas sensing unit;
(d) continuously monitoring and sensing the ambient gas in the area established by said placing step;
(e) periodically segregating a sample of ambient gas being continuously monitored and sensed;
(f) flowing in a first flowing step said segregated sample through said first gas sensing area and then into said second gas sensing area;
(g) flowing in a second flowing step said segregated sample through said second gas sensing area and then into said first gas sensing area;
(h) periodically measuring the signal from said sensor unit in response to the gas present in said sample of the ambient by controlling and measuring the flow of said sample in said first and second flowing steps;
(i) establishing the concentration of any sensed gas in said sample from said controlling and measuring step;
(j) inserting the values obtained from said signal controlling and measuring and concentration establishing steps into said automatic control; and
(k) converting the values from said inserting step into the continuous sensing and monitoring readings of said sensor unit.

5. The method of claim 4, further characterized by the steps of
(a) preselecting a periodic interval for recalibrating said gas sensor unit; and
(b) entering said preselected period into said automatic control.

6. The method of claim 4, further characterized by
(a) said concentration establishing step is carried out by segregating and measuring coulometrically a preselected quantity of the gas being monitored.

7. The method of claim 4, further characterized by
(a) providing an electrochemical gas generating cell;
(b) connecting said gas generating cell to said gas sensor unit; and
(c) supplying gas of unknown concentration from said gas generating cell for said concentration establishing, signal measuring, and converting steps.

* * * * *